(12) United States Patent
Sierra

(10) Patent No.: US 10,667,964 B2
(45) Date of Patent: *Jun. 2, 2020

(54) REUSABLE HOLDER FOR ABSORBENT MATERIAL

(71) Applicant: Be Girl, Inc., Brooklyn, NY (US)

(72) Inventor: Diana Beatriz Sierra, North Bergen, NJ (US)

(73) Assignee: BE GIRL, INC., Brooklyn, NY (US)

( * ) Notice: Subject to any disclaimer, the term of this patent is extended or adjusted under 35 U.S.C. 154(b) by 982 days.

This patent is subject to a terminal disclaimer.

(21) Appl. No.: 15/162,269

(22) Filed: May 23, 2016

(65) Prior Publication Data

US 2016/0262960 A1 Sep. 15, 2016

Related U.S. Application Data

(63) Continuation of application No. 14/057,802, filed on Oct. 18, 2013, now Pat. No. 9,433,543.

(60) Provisional application No. 61/715,890, filed on Oct. 19, 2012.

(51) Int. Cl.
*A61F 13/66* (2006.01)
*A61F 13/74* (2006.01)

(52) U.S. Cl.
CPC ............ *A61F 13/665* (2013.01); *A61F 13/74* (2013.01)

(58) Field of Classification Search
CPC ........ A61F 13/66; A61F 13/665; A61F 13/68; A61F 13/70; A61F 13/72; A61F 13/74; A61F 13/76; A61F 13/80; A61F 13/82
See application file for complete search history.

(56) References Cited

U.S. PATENT DOCUMENTS

| | | | | |
|---|---|---|---|---|
| 5,733,275 | A * | 3/1998 | Davis | A61F 13/5605 604/387 |
| 9,433,543 | B2 * | 9/2016 | Sierra | A61F 13/665 |
| 2004/0236298 | A1 * | 11/2004 | Coates | A61F 13/476 604/385.04 |
| 2011/0213326 | A1 * | 9/2011 | Tournier | A61F 13/15268 604/385.14 |

FOREIGN PATENT DOCUMENTS

GB         2258403 A * 2/1993 ......... A61F 13/5121

* cited by examiner

*Primary Examiner* — Peter S Vasat
(74) *Attorney, Agent, or Firm* — Duane Morris LLP; Thomas J Kowalski; Deborah L. Lu

(57) ABSTRACT

A reusable holder for absorbent material for absorbing menstrual flow is made from a liquid permeable inner layer affixed to an outer liquid impermeable layer at the peripheral edges to form a pouch between the two layers. An opening in the inner layer provides access to the pouch so that disposable or reusable absorbent material such as paper or cloth may be placed in the pouch to absorb menstrual flow. After use, the absorbent material may be removed from the pouch via the opening so that the used absorbent material may be disposed of or washed for re-use. Wings extending from the sides of the reusable holder allow the holder to be fastened around an undergarment to keep the holder in place. Alternatively, strings are attached to the reusable holder to allow it to be worn like a g-string.

15 Claims, 5 Drawing Sheets

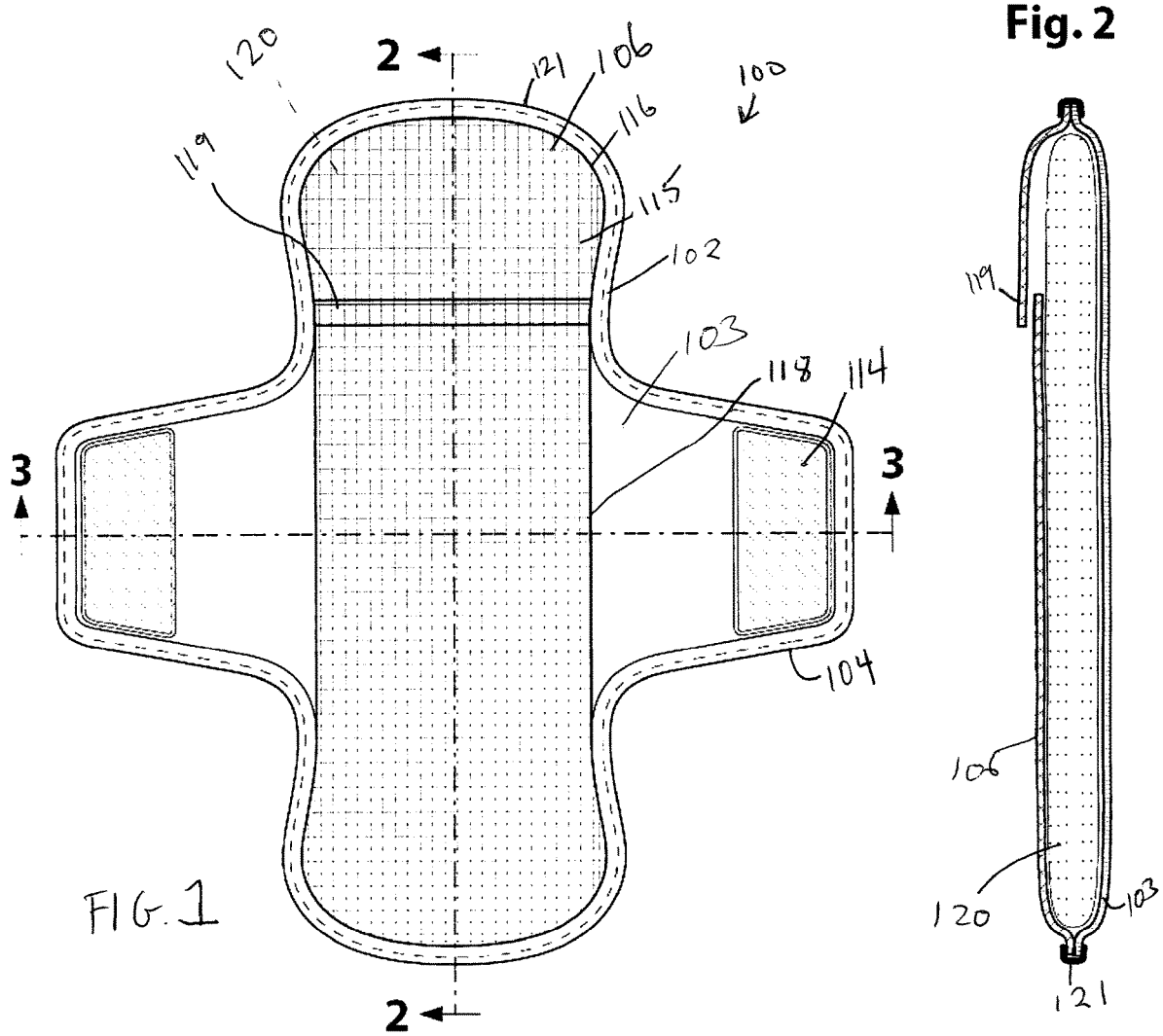
Fig. 2
FIG. 1
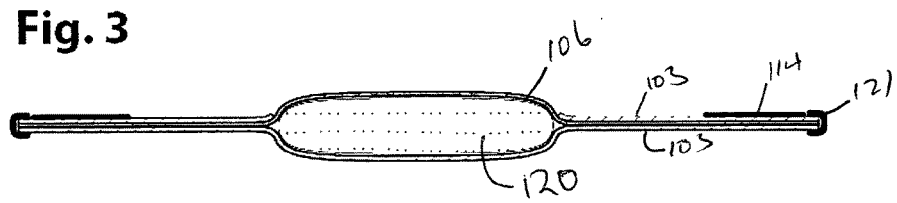
Fig. 3

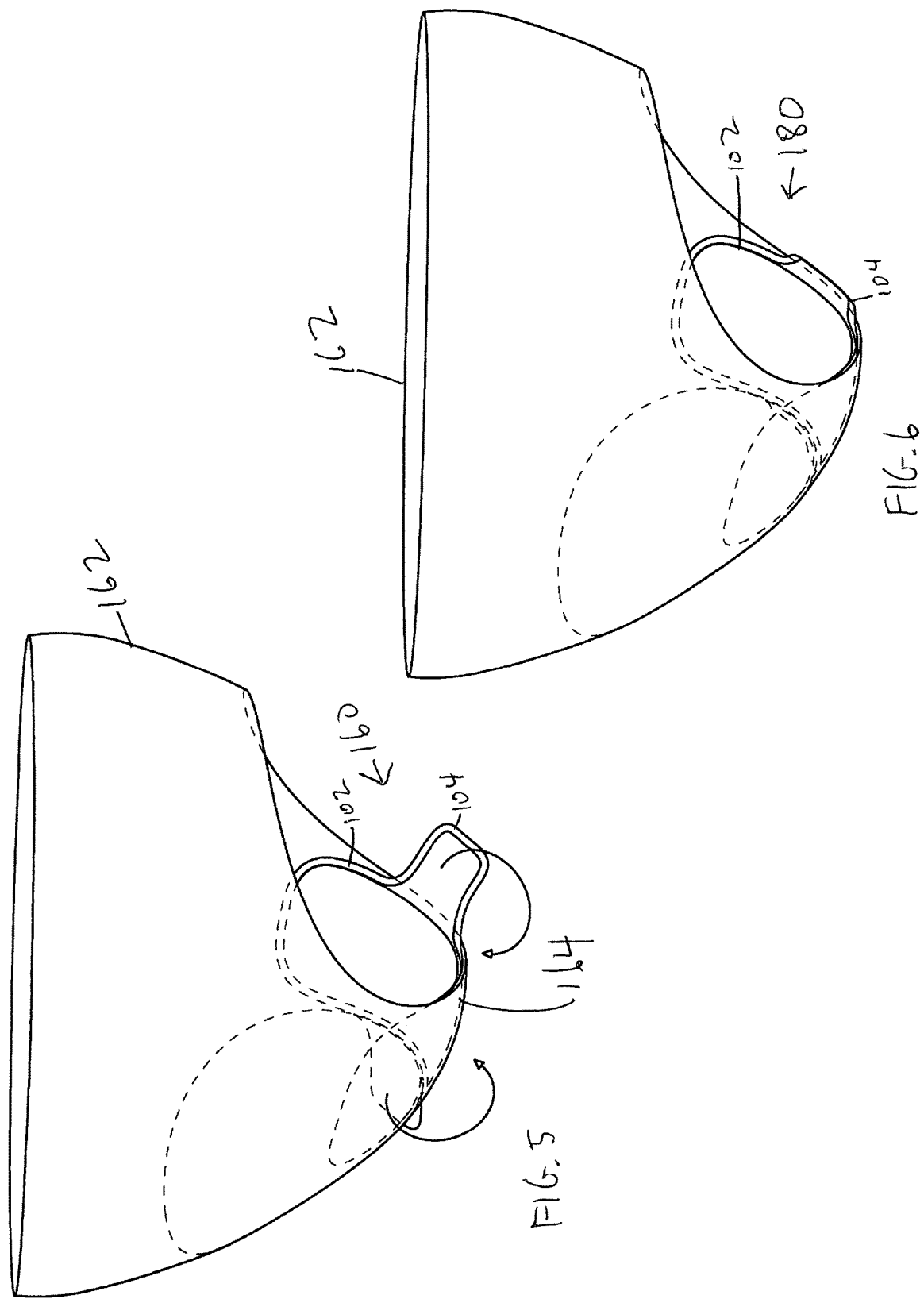

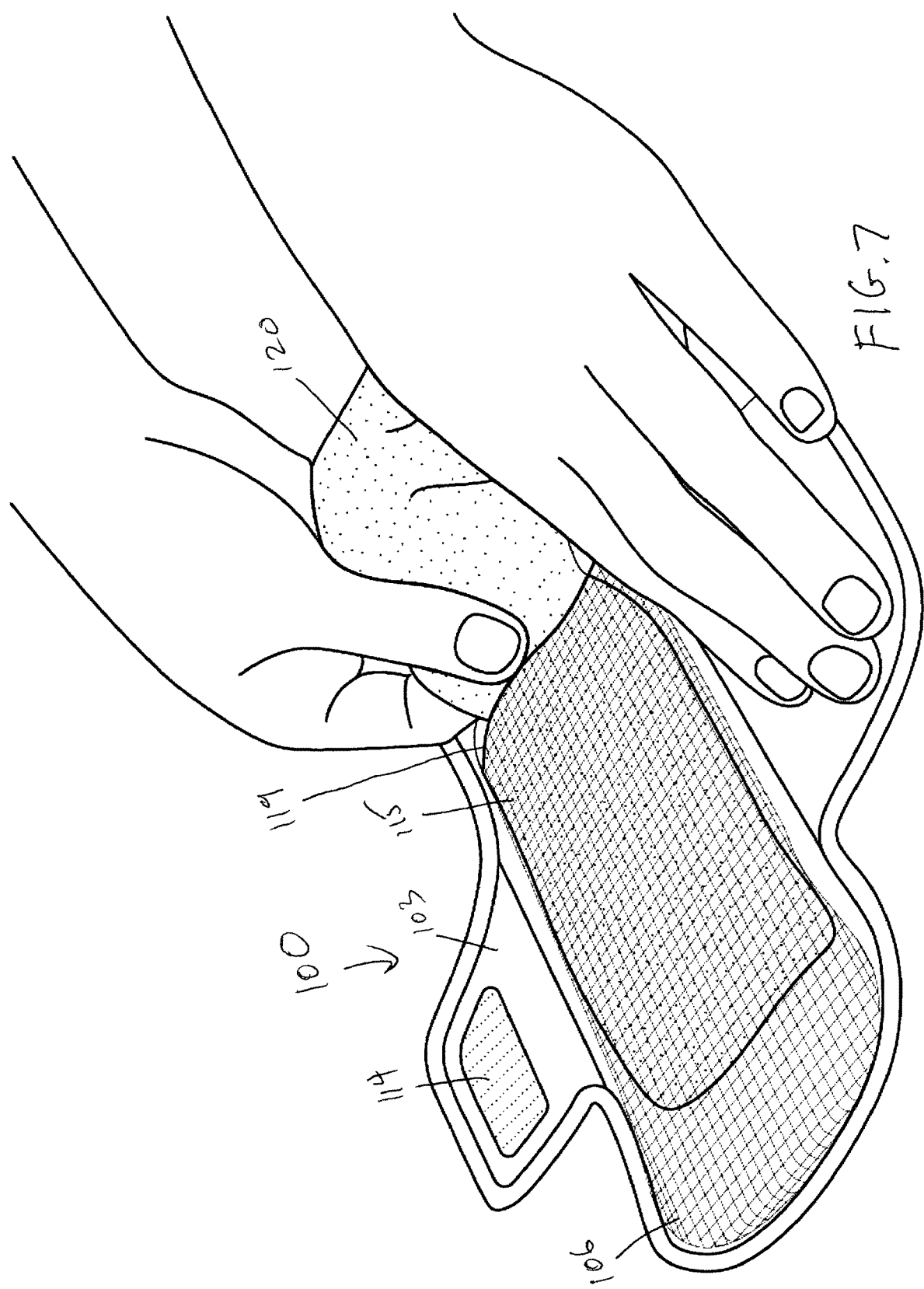

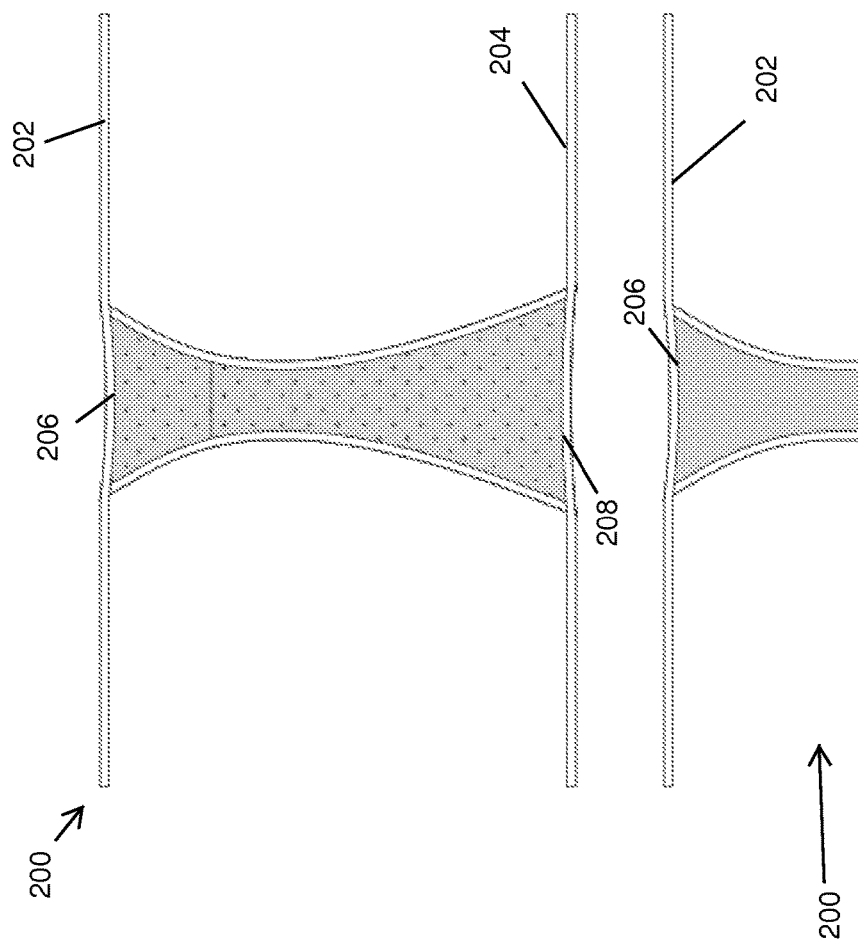

REUSABLE HOLDER FOR ABSORBENT MATERIAL

RELATED APPLICATIONS

This U.S. patent application is a continuation of prior application Ser. No. 14/057,802, filed Oct. 18, 2013, now U.S. Pat. No. 9,433,543, which claims the benefit of and expressly incorporates by reference all of the disclosure of U.S. Provisional Application No. 61/715,890 of the same inventor, entitled "Pad Holder", filed Oct. 19, 2012.

FIELD OF INVENTION

This U.S. patent application is directed to sanitary pads, and more specifically, to a reusable holder allowing the use of reusable or disposable for absorbent materials for absorbing menstrual flow.

BACKGROUND

Sanitary pads are absorbent items worn by women when they are menstruating. They generally comprise an absorbent portion for absorbing liquid and may also include a mechanism for attachment or holding the pad in place. Sanitary pads may be worn with an undergarment.

In the past, materials such as knitted pads and menstrual aprons have been used during menstruation. Rags consisting of folded old cloth were previously used as well.

The advent of disposable sanitary pads was a marked improvement over the technologies that existed prior. Used primarily in more affluent countries such as those in the western world and in other parts of the world, disposable feminine sanitary pads provide numerous benefits, including hygienic, comfort, ease of use and other benefits. Unfortunately, the one-time use nature of a disposable sanitary pad means that the cost of such pads is relatively high. Manufacturers take steps to reduce cost, but the disposable nature of a one-time use sanitary pad means that users must continually spend money to purchase new pads.

In disadvantaged countries and communities, personal income may be so low that disposable sanitary pads are simply not an option for purchase. Many women in such areas have to use discarded cloths or rags, or must simply improvise a sanitary pad out of materials such as paper, weeds, grass, clothes, or rags, or other such materials. As might be imagined, these materials may not provide a desired level of effectiveness, comfort, or safety. Further, they may not be readily available. Also, even if materials such as cloth or rags available, the lack of clean water in many poor disadvantaged countries prevents these improvised sanitary napkins from being properly washed to allow re-use.

The difficulties experienced by women in these situations may cause them to fail to attend school or work. It is unfortunate that an issue which is so readily solved in more affluent countries presents such difficulties for less fortunate women. A satisfactory solution to this problem therefore is a highly important issue which must be solved. The disclosure presented herein provides an affordable, easy, and cheap to manufacture solution to these problems.

SUMMARY OF INVENTION

The foregoing purposes, as well as others that will be apparent are achieved generally by a reusable pad holder or holder (hereafter, "reusable holder or "holder") for absorbent materials for absorbing menstrual flow. The holder comprises a liquid permeable inner layer and an outer layer that are affixed together at the peripheral edges to form a pouch. An opening in the inner layer allows reusable or disposable absorbent material such as paper or cloth to be inserted into the pad to absorb menstrual flow. The absorbent material may be removed after use and replaced with new absorbent material. Wings extending from the pad serve to hold the pad in place by hugging or wrapping around a user's undergarment. Alternatively, instead of wings the holder may have strings each end which are tied around the user's waist so that the holder can be worn like a bikini bottom or g-string. Other objects, features, and advantages of the present disclosure will be apparent when the detailed description is considered in conjunction with the following drawings.

BRIEF DESCRIPTION OF DRAWINGS

Various embodiments will be hereinafter described with reference to drawings for the purpose of illustrating the foregoing and other aspects of the disclosure.

FIG. 1 is a top-down view of a reusable holder according to one embodiment of the present disclosure.

FIG. 2 is a cross-sectional view of the holder of FIG. 1, taken along lines 2-2.

FIG. 3 is a cross-sectional view of the holder of FIG. 1, taken along 3-3.

FIG. 5 is a front view of the holder of FIG. 1 mounted on an undergarment with the holder in an open position.

FIG. 6 is a front view of the holder of FIG. 5 with the holder in a closed position.

FIG. 7 is a perspective view of the holder of FIG. 1, showing absorbent material being inserted into a pouch in the holder.

FIG. 8 is top view of an alternate embodiment of a holder.

FIG. 9 is a bottom view of the holder of FIG. 8.

DETAILED DESCRIPTION OF EMBODIMENTS OF INVENTION

Figure 4:
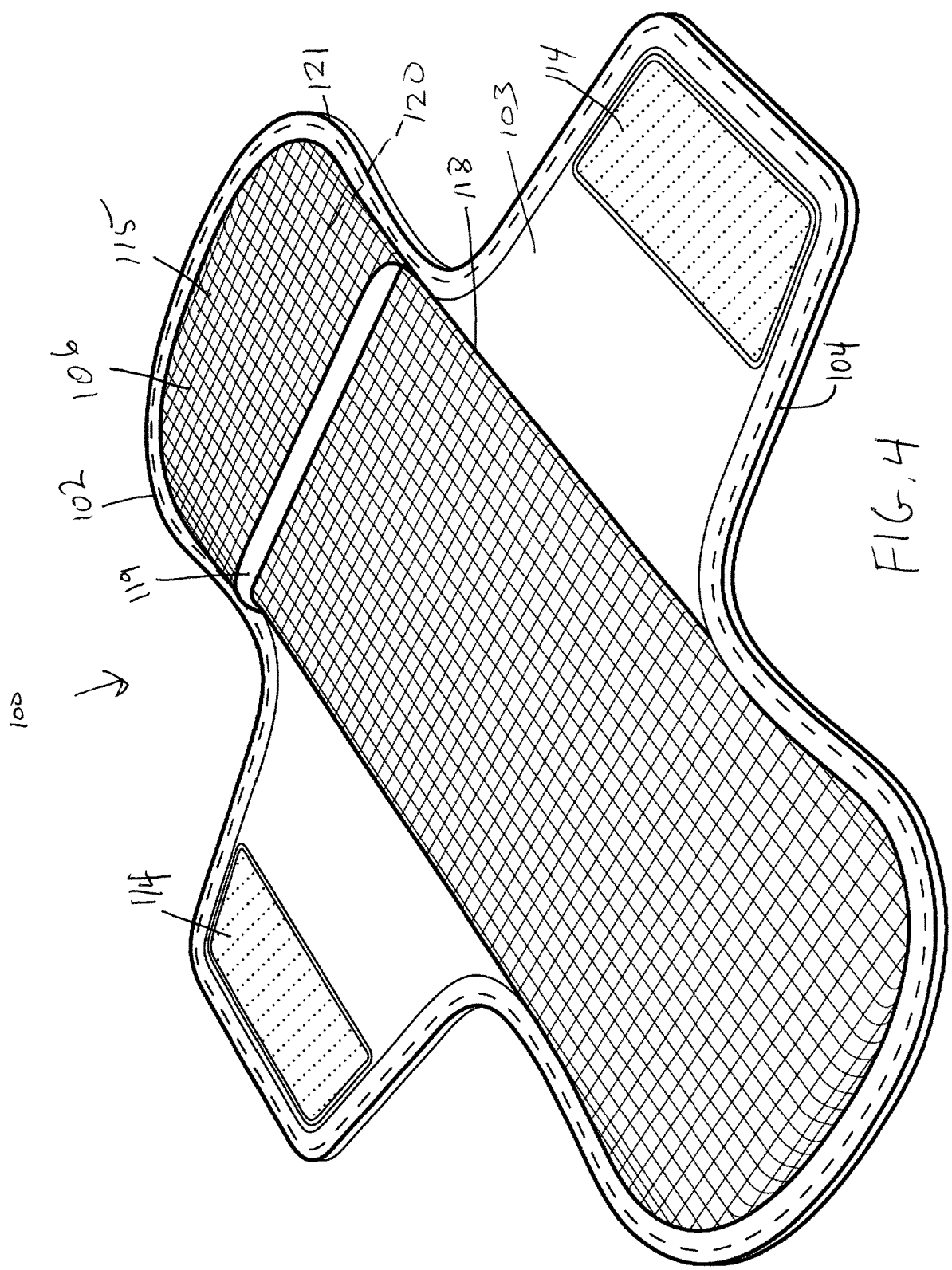
FIG. 4 is a perspective view of the holder of FIG. 1.

Various embodiments will be hereinafter described with reference to drawings for the purpose of illustrating the foregoing and other aspects of the disclosure.

Referring to FIGS. 1-4, holder 100 comprises a body 102, an outer layer 103, and a liquid permeable inner layer 106. As used herein, the term "inner" means the direction facing the body of the user while the term "outer" means the direction facing away from the user's body. In the present embodiment, liquid permeable inner layer 106 is a nylon mesh fabric. Alternative materials are polyester, cotton, and natural and synthetic fiber mesh. Outer layer 103 is preferably liquid impermeable. In the present embodiment, outer layer 103 is made of waterproof nylon fabric. Alternative materials are polyester, polyurethane, and any natural or synthetic fabrics that are laminated to or coated with a waterproofing material.

Inner layer 106 is coupled, joined, or affixed to outer layer 103, along a peripheral track 118, over a central portion 116 of the body 102, such that a pouch 115 is formed above central portion 116 and between the inner and outer layers 106, 103. In the present embodiment, inner layer 106 is joined or affixed to outer layer 103 by a sewn joint. Other methods such as gluing, heat, or fabric adhesives may also be used.

Inner layer 106 has an opening 119 such as a slit which provides access to pouch 115 for insertion of an absorbent material 120. (FIGS. 1-4) The liquid permeability of inner layer 106 allows for liquid to flow through inner layer 106 into absorbent material 120 while holder 100 is in a worn position. Specifically, absorbent material 120 absorbs menstrual flow and other fluids when holder 100 is in position in an undergarment 162 (FIGS. 5-6) such as a pair of panties. Opening 119 also allows for the removal of absorbent material 120 (e.g., toilet paper) for disposal after use. Alternatively, if the absorbent material 120 is cloth or other washable material, the soiled cloth may be removed for cleaning and re-use. Opening 119 and pouch 115 allows the user to insert and remove any absorbent material into pouch 115. Examples of absorbent material 120 are cloth, paper (e.g. toilet paper), gauze, and processed/pretreated absorbent natural fibers such as banana bark, sisal, and cotton.

A lining 121 (FIGS. 1-3) is also provided around the periphery of holder 100. Lining 121 is provided to ensure a comfortable interface between holder 100 and the wearer, and helps to prevent any irritation which may be caused by contact between any rough edges of holder 100 and the wearer. Lining 121 preferably traces the perimeter of holder 100, including wings 104. In the present embodiment, lining 121 is made of cotton although other natural materials which provide similar functionality such as rayon, linen, silk, or man-made fabric alternatives such as Lyocell and Modal® may also be used.

The holder 100 may be held in place by the use of wings 104 extending from central portion 116 of body 102. Wings 104 preferably have a clasping or attachment mechanisms 114 such as Velcro®, buttons, snaps, hook and loop fasteners or other similar devices. In the present embodiment, the attachment mechanism is Velcro®. Attachment mechanism 114 allows holder 100 to be held in place while worn. Preferably, wings 104 are wrapped around a portion 164 of an undergarment 162 and attachment mechanism 114 is engaged to keep the holder 100 in place. (FIGS. 4-6) This position is called the closed position 180 and is shown in FIG. 6. The open position 160, in which wings 104 are not engaged is shown in FIG. 5. In the present embodiment (FIG. 3) wings 104 are extensions of outer layer 106 and inner layer 103 from central portion 116 of body 102 wherein the extension of inner layer 103 is tucked between the extension of outer layer 103.

In an alternative embodiment (FIGS. 8-9), if the wearer or user does not have access to undergarments, the wings may be replaced by two long strings 202, 204 attached respectively to a front end 206 and a back end 208 of a holder 200. Strings 202, 204 are tied around the waist of the wearer or user so that holder 200 can be worn like a G-string or bikini bottom.

Although the invention has been described with reference to preferred embodiments, it will be appreciated by one of ordinary skill in the art that numerous configurations and modifications are possible in light of the above disclosure. All such variations and modifications are intended to be within the scope of the invention.

The invention claimed is:

1. A reusable undergarment,
for a human female user,
comprising:
a holder having:
an inner layer that faces the body of the human female user,
an outer layer that faces away from the human female user's body
a front end,
a back end,
a middle section positioned approximately equidistant between the front end and the back end, and
a first string connected to the front end and a second string connected to the back end, whereby the first and second strings are configured to be tied around the human female user's waist when the undergarment is in use,
wherein:
the outer layer is comprised of a fluid impermeable material,
the inner layer is liquid permeable,
the inner layer is affixed to the outer layer along a peripheral edge of the inner layer so as to form a pouch between the inner layer and the outer layer, and the peripheral edge defining opposing longitudinal edges and opposing end edges of the pouch,
the inner layer has an opening positioned approximately equidistant between the middle section and the front end and transverse to the longitudinal edges of the pouch, thereby for providing access to the pouch, and the inner layer comprising first and second pieces of mesh fabric, the second piece overlapping the first piece at the opening, whereby the pouch is configured for insertion and removal of absorbent material, and
the undergarment is configured to be worn by the human female user, and
the undergarment is for collecting fluid from the human female user when in use.

2. The undergarment of claim 1, further comprising the absorbent material.

3. The undergarment of claim 1, additionally comprising a lining along and around a periphery of the holder.

4. The undergarment of claim 1, wherein the mesh fabric comprises nylon.

5. The undergarment of claim 1, wherein the mesh fabric comprises polyester.

6. The undergarment of claim 1, wherein the fluid from the human female user comprises menstrual flow.

7. The undergarment of claim 1 wherein the opening comprises a slit.

8. A reusable holder of absorbent material,
for affixing to a human female user's panties,
comprising:
an inner layer that faces the body of the human female user,
an outer layer that faces away from the human female user's body
a front end,
a back end,
a middle section positioned approximately equidistant between the front end and the back end, and
a pair of wings,
each wing:
extending transversely from the outer layer at the middle section, along opposing lengths of the outer layer, and
each wing:
comprising an attachment mechanism disposed at a distal end, for attaching the wings to each other,
wherein:
the outer layer is comprised of a fluid impermeable material,
the inner layer is liquid permeable,
the inner layer is affixed to the outer layer along a peripheral edge of the inner layer so as to form a pouch between the inner layer and the outer layer, and the peripheral edge defining opposing longitudinal edges and opposing end edges of the pouch, the inner layer has an opening positioned approximately equidistant between the middle section and the front end and transverse to the longitudinal edges of the pouch, thereby for providing access to the pouch, and the inner layer comprising first and second pieces of mesh fabric, the second piece overlapping the first piece at the opening, whereby the pouch is configured for insertion and removal of absorbent material, the holder is for affixing to the human female user's panties who is at least of age to be menstruating, the holder is configured and sized for affixing to the human female user's panties and the holder is for collecting fluid from the human female user when in use.

9. The holder of claim 8, further comprising the absorbent material.

10. The holder of claim 8, additionally comprising a lining along and around a periphery of the holder.

11. The holder of claim 8, wherein the mesh fabric comprises nylon.

12. The holder of claim 8, wherein the mesh fabric comprises polyester.

13. The holder of claim 8, wherein the fluid from the human female user comprises menstrual flow.

14. The holder of claim 8 wherein the opening comprises a slit.

15. The holder of claim 8, further comprising a pair of panties.

* * * * *